US00PP25752P3

(12) United States Plant Patent
Schoone

(10) Patent No.: US PP25,752 P3
(45) Date of Patent: Jul. 28, 2015

(54) ***PHALAENOPSIS* ORCHID PLANT NAMED 'FLOR167725'**

(50) Latin Name: *Phalaenopsis hybrida*
Varietal Denomination: FLOR167725

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 120 days.

(21) Appl. No.: 13/986,271

(22) Filed: Apr. 18, 2013

(65) Prior Publication Data

US 2013/0291244 P1 Oct. 31, 2013

Related U.S. Application Data

(60) Provisional application No. 61/638,224, filed on Apr. 25, 2012.

(51) Int. Cl.
*A01H 5/00* (2006.01)
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

(56) References Cited

U.S. PATENT DOCUMENTS

PP12,639 P2 * 5/2002 Arndt ..... Plt./311

OTHER PUBLICATIONS

The International Orchid Register / RHS Gardening 2014, retrieved on Oct. 1, 2014, retrieved from the Internet at <http://apps.rhs.org.uk/horticulturaldatabase/orchidregister/orchiddetails.asp?ID=43524> for *Phalaenopsis* 'Summertime', 7 pp.*

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'FLOR167725' particularly characterized by flowers which are yellow/green, the labellum is yellow with some white; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'FLOR167725'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'FLOR167725'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'FLOR167725' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'FLOR167725' originated from a cross made by the inventor in 1999 in Strengweg, Heemskerk, The Netherlands. The female or seed parent is the *Phalaenopsis* cultivar designated 'Oxford', unpatented. The male or pollen parent is the *Phalaenopsis* cultivar designated 'amabilis', unpatented. The new *Phalaenopsis* 'FLOR167725' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture (mericloning) was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'FLOR167725', which in combination distinguish this *Phalaenopsis* as a new and distinct cultivar:

1. flowers which are yellow/green, the labellum is yellow with some white;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'FLOR167725', the female parent 'Oxford' has yellow flowers which are about 10 cm high and the male parent 'Amabilis' has white colored flowers which are about 7 cm high, whereas the flowers of 'FLOR167725' are yellow/green and about 6 cm high.

Presently, a commercial cultivar to which 'FLOR167725' can be meaningfully compared is 'Anthura Gold' (Patented, U.S. Plant Pat. No. 12,639). The plant size and the raceme of 'FLOR167725' are larger than 'Anthura Gold'. The flower of 'Anthura Gold' is light yellow with at the base some darker yellow spots, whereas the flower of 'FLOR167725' is yellow/green with at the base some grey/orange spots.

BRIEF DESCRIPTION OF THE PHOTOGRAPHS

The accompanying photographs illustrate the overall appearance of the new *Phalaenopsis* 'FLOR167725' showing the colors as true as is reasonably possible with colored reproductions of this type. Colors in the photographs may differ slightly from the color values cited in the detailed botanical description, which accurately describe the color of 'FLOR167725'.

DETAILED BOTANICAL DESCRIPTION

Figure 1:
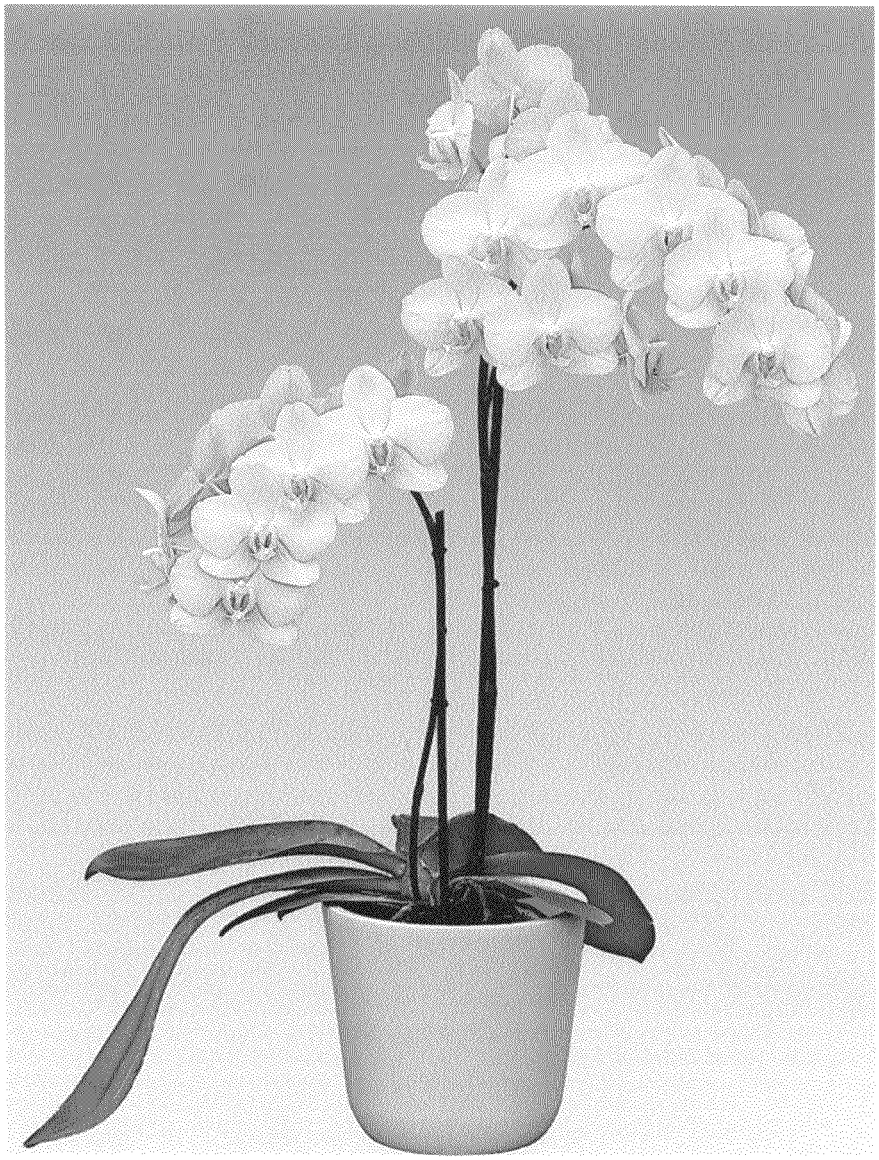
FIG. 1 shows a side view perspective of a typical flowering plant of 'FLOR167725' in a 12 cm pot, at 16 months of age.

The new *Phalaenopsis* cultivar 'FLOR167725' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'FLOR167725' as grown in a greenhouse in Strengweg, Heemskerk, The Netherlands, under conditions which closely approximate those generally used in commercial practice. Initially, the ideal temperature to grow plants of 'FLOR167725' is 27° C. during the day and at night. Then, during the flowering phase of 'FLOR167725', the ideal growing temperature is 20-22° C. during the day and 18° C. at night. Light levels for growing 'FLOR167725' are a minimum of 5,000 lux and a maximum of 10,000 lux. A balanced fertilizer with level of 200 ppm N, 87 ppm P, 168 ppm K is applied. Duration of growth of 'FLOR167725' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'FLOR167725' plants described is 12 months after potting.

Classification:

*Botanical.—Phalaenopsis hybrida.* parentage:

*Female or seed parent.—Phalaenopsis* cultivar designated 'Oxford', unpatented.

*Male or pollen parent.—Phalaenopsis* cultivar designated 'amabilis', unpatented.

Propagation:

*Type*.—Tissue culture.

*Rooting habit and description*.—Fleshy; approximately 3 mm-7 mm wide and green in color (RHS 195C and RHS 138A); freely branching. It takes 12 weeks for plants growing in tissue culture to initiate roots.

Plant:

*Size at maturity*.—Height: about 59 cm. Spread: about 64 cm.

*Growth habit*.—Small; dark green leaves (RHS 137A) and a relatively normal raceme.

*Vigor*.—Moderate.

*Crop time*.—Following asexual propagation, at about 26 weeks 2 leaves appear; at about 30 weeks 3-4 leaves appear; after a cold treatment of about 4-8 weeks at a temperature of about 19° C. about 1-3 racemes with flowers appear.

Foliage:

*Quantity per plant*.—About 6 to 8 leaves are produced before flowering.

*Arrangement and attachment*.—Half up/horizontal and on two sides.

*Overall shape of leaf*.—Oval, slightly point tip and asymmetric.

*Texture (upper & underside)*.—Smooth and leathery.

*Pubescence*.—None.

*Mature leaf length*.—About 11 to 29 cm.

*Mature leaf width*.—About 6 to 9 mm.

*Mature leaf thickness*.—About 2 mm.

*Mature leaf color*.—Upper side: green (RHS 137A). Under side: green (RHS 144A).

*Leaf base*.—Acute.

*Margin*.—Entire.

*Venation*.—Pattern: parallel. Color of midvein: upper side: green (RHS N137A). Under side: yellow/green (RHS N144C).

Inflorescence description:

*Appearance*.—Upright to slightly pendant, racemose inflorescence with bilaterally symmetrical flowers that open in succession beginning with the lowermost flower.

Raceme:

*Quantity per plant*.—About 1 to 3.

*Number of flowers per raceme*.—About 7 to 17.

*Length*.—About 44 to 62 cm.

*Peduncle*.—Diameter: about 3 mm. Strength: strong. Aspect: upright. Texture: glabrous and smooth. Color: RHS 146A.

*Buds*.—Height (from base to tip): about 20 mm. Diameter (at midpoint): about 18 mm. Shape: egg-shaped, with a lump on the side. Color: yellow/green (RHS 150B) with a grey/orange haze (RHS 173A).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-3 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
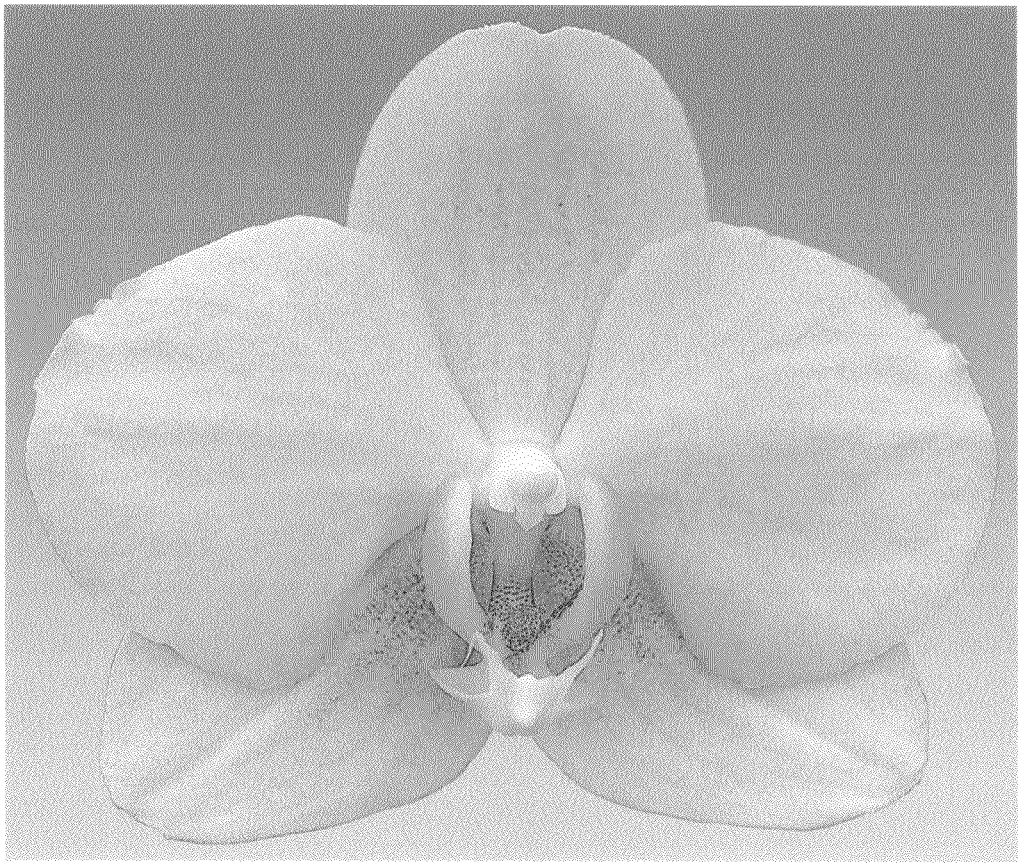
FIG. 2 shows a close-up view of a typical flower of 'FLOR167725'.
Figure 3:
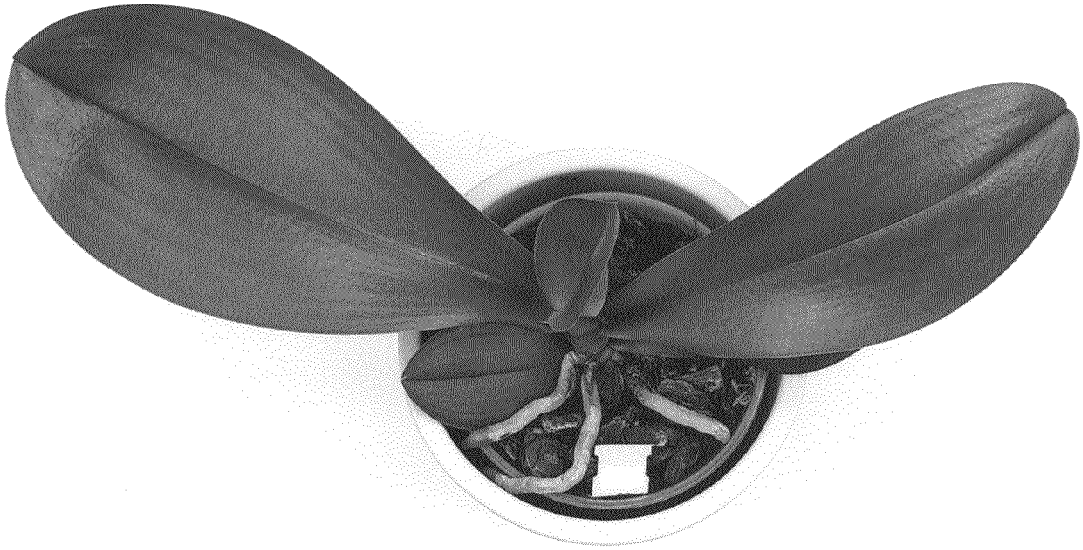
FIG. 3 shows a close-up view of the typical leaves of 'FLOR167725'.

*Flower*.—Rate of opening: Flowers fully opened about 2 to 3 days after petal and sepal separation. Orientation at opening: slanted upward and outward. Shape: typical shape of *Phalaenopsis* orchid; see FIG. 2. Size (of single bloom): Height: about 46 mm to 69 mm. Diameter: about 55 mm to 76 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate. Apex: broadly obtuse with a notch. Margin: entire and weakly undulate. Base: broadly ovate. Length: about 28 mm to 41 mm. Width: about 25 mm to 35 mm. Texture: Upper surface: smooth and satiny. Under surface: smooth and satiny. Color (when fully opened): upper side: yellow/green (RHS 154C) with thin yellow/green veins (RHS 154B). At the bottom some hazy grey/orange spots (RHS 173C). At the base some white (RHS NN155B). Under side: yellow/green (RHS 154C). At the bottom some white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it. Margin: entire and weakly undulate. Apex: oval. Length midlobe: about 16 mm. Width (not flattened) midlobe: about 13 mm. Length lateral lobe: about 15 mm. Width (not flattened) lateral lobe: 8 mm. Depth of tube created by lateral lobes of labellum: about 4 mm. Texture: Upper and under surface: smooth and satiny. Color (when fully opened): Midlobe: upper surface: main color is yellow (RHS 12A). In the center a yellow line (RHS 13A). At the base some grey/orange spots (RHS N172C). Close to the cirrhi some white (RHS NN155C). Under surface: white (RHS NN155D). The edges are green/yellow (RHS 1A). In between some yellow (RHS 6A). Lateral lobes: upper surface: white (RHS NN155D). The outer edge is yellow (RHS 12A). At the base a haze of yellow/orange (RHS 14A) with on top spots and stripes (RHS 59B). Under side: white (RHS NN155D). Outer edge is yellow (RHS 12A). Cirrhi: short (about 6 mm) and curly. Color: yellow (RHS 12A). Pestle (Callosities): Length: about 4 mm. Width (not flattened): about 4 mm. Color: yellow/orange (RHS 14A) with grey/orange spots (RHS N172A).

*Sepals*.—Arrangement: Outer whorl comprises 3 sepals: one dorsal sepal and two lateral sepals. Overall shape: elliptical and weakly cupped. Margin: entire and weakly undulate. Length: about 33 mm. Width: about 29 mm. Apex: lateral: oval with a little point; dorsal: oval with little gap. Texture: Upper and under surface: smooth and satiny. Color (when fully opened): upper surface: main color is yellow/green (RHS 154C) with small yellow/green veins (RHS 154A). At the bottom of the dorsal sepal hazy spots grey/orange (RHS 173C). At the lateral sepals the spots (RHS 1738) and at the base some white (RHS NN155D with red/purple (RHS 65B). Under surface dorsal and lateral: main color is yellow/green (RHS 150B). At the bottom yellow/green (RHS 150C). At the base a red/purple haze (RHS 65D).

*Pedicel*.—Length: about 20 mm to 31 mm. Diameter: about 3 mm. Texture: glabrous and smooth. Color: at the base yellow/green (RHS 145B) and close to flower yellow/green (RHS 154C).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 5 mm. Color: white (RHS 155C). Pollinia: Quantity: two. Diameter: about 1 mm. Color: orange (RHS 26A).

*Ovary*.—Length: about 2 mm. Diameter: about 1.5 mm. Color: white (RHS 155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'FLOR167725', as illustrated and described herein.

* * * * *